United States Patent
Van Berkel

(10) Patent No.: US 12,082,941 B2
(45) Date of Patent: *Sep. 10, 2024

(54) MONITORING BONE CHARACTERISTICS

(71) Applicant: KONINKLIJKE PHILIPS N.V., Eindhoven (NL)

(72) Inventor: Joep Van Berkel, Gronsveld (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 320 days.

This patent is subject to a terminal disclaimer.

(21) Appl. No.: 17/589,828

(22) Filed: Jan. 31, 2022

(65) Prior Publication Data

US 2022/0151546 A1    May 19, 2022

Related U.S. Application Data

(63) Continuation of application No. 16/315,183, filed as application No. PCT/EP2017/066981 on Jul. 6, 2017, now Pat. No. 11,234,636.

(30) Foreign Application Priority Data

Jul. 6, 2016  (EP) ..................... 16178132

(51) Int. Cl.
*A61B 5/00*  (2006.01)
*A61B 8/08*  (2006.01)
(Continued)

(52) U.S. Cl.
CPC .......... *A61B 5/4547* (2013.01); *A61B 5/0022* (2013.01); *A61B 5/0075* (2013.01);
(Continued)

(58) Field of Classification Search
CPC ... A61B 5/0022; A61B 5/0075; A61B 5/0082; A61B 5/0088; A61B 5/0095;
(Continued)

(56) References Cited

U.S. PATENT DOCUMENTS 4,913,157 A    4/1990  Pratt, Jr. et al.
2002/0161300 A1   10/2002  Hoff et al.
(Continued)

FOREIGN PATENT DOCUMENTS

DE    102011056867 A1    6/2013
EP         0772999 A2    5/1997
(Continued)

OTHER PUBLICATIONS

Figueiredo et al: "Characterization of Bone and Bone-Based Graft Materials Using FTIR Spectroscopy"; Chapter 18, Infrared Spectroscopy-Life and Biomedical Sciences, Tehophanides Theophile, (Ed.), ISBN:978-953-51-0537-1, Apr. 2012; pp. 315-338.
(Continued)

*Primary Examiner* — George Manuel

(57) ABSTRACT

The present disclosure is directed to methods and apparatus for monitoring bone characteristics for various conditions such as osteoporosis and/or periodontitis. In various embodiments, a dental hygiene appliance (100) may include: a handle (102) adapted to be held by a user; a tool (106) secured to the handle to perform a dental hygiene-related task; emitter(s) (114A, 116, 360A) mounted on the dental hygiene appliance to emit wave(s) (252, 362) towards a mandible (250, 350) of the user; sensor(s) (114B, 116, 360B) mounted on the dental hygiene appliance to detect wave(s) (254, 364) propagating away from the mandible, wherein the detected wave(s) originate from or are caused by the emitted wave(s); and a controller (108) communicatively coupled with the emitter(s) and the sensor(s). The controller may: receive, from the sensor(s), signal(s) indicative of the detected waves; and determine, based on the signal(s), bone characteristic(s) of the user.

14 Claims, 6 Drawing Sheets

(51) Int. Cl.
*A61C 17/22* (2006.01)
*A61C 19/04* (2006.01)

(52) U.S. Cl.
CPC .......... *A61B 5/0082* (2013.01); *A61B 5/0095* (2013.01); *A61B 5/4509* (2013.01); *A61B 5/6898* (2013.01); *A61B 5/7257* (2013.01); *A61B 5/7264* (2013.01); *A61B 5/7275* (2013.01); *A61B 8/0875* (2013.01); *A61C 17/225* (2013.01); *A61C 19/04* (2013.01)

(58) Field of Classification Search
CPC ... A61B 5/4509; A61B 5/4542; A61B 5/4547; A61B 5/6898; A61B 5/7257; A61B 5/7264; A61B 5/7275; A61B 8/0875; A61C 17/16; A61C 17/22; A61C 17/225; A61C 19/04
See application file for complete search history.

(56) References Cited

U.S. PATENT DOCUMENTS

| | | |
|---|---|---|
| 2005/0070797 A1 | 3/2005 | Cadossi et al. |
| 2006/0192965 A1 | 8/2006 | Tromberg et al. |
| 2007/0133739 A1 | 6/2007 | Hangartner et al. |
| 2008/0060148 A1 | 3/2008 | Pinyayev et al. |
| 2012/0046536 A1* | 2/2012 | Cheung .................. A61B 34/20 600/407 |
| 2012/0244489 A1 | 9/2012 | Carnahan |
| 2013/0080295 A1 | 3/2013 | Dykes et al. |
| 2013/0091642 A1 | 4/2013 | Dykes et al. |
| 2015/0108836 A1 | 4/2015 | Hsu |
| 2016/0331301 A1 | 11/2016 | Radmand |

FOREIGN PATENT DOCUMENTS

| | | |
|---|---|---|
| JP | 2013116293 A | 6/2013 |
| WO | 03047451 A2 | 6/2003 |
| WO | 2007004604 A1 | 1/2007 |

OTHER PUBLICATIONS

Martinez-Maestre et al: "Periodontitis and Osteoporosis: A Systematic Review"; Climacteric, vol. 13:6, pp. 523-529, 2010.

Paschalis et al: "Infrared Assessment of Bone Quality: A Review"; Clin Orthop Relat Res, (2011), vol. 469 (8), pp. 2170-2178.

Straka et al: "Periodontitis and Osteoporosis"; Neuroendocrinology Letters, vol. 36(5), 2015, pp. 401-406.

Tawackoli et al: "Vibrational Analysis of Normal and Osteopenic Trabecular Bone Using Rapid Prototyped Duplicates"; ISB XXTH Congress—ASB 29th Annual Meeting, Jul. 31-Aug. 5, 2005, Cleveland, Ohio, p. 826.

Wade et al: "Estimating Prevalence of Osteoporosis: Examples From Industrialized Countries"; Archives of Osteoporosis (2014), vol. 9:182, pp. 1-10.

* cited by examiner

MONITORING BONE CHARACTERISTICS

CROSS-REFERENCE TO PRIOR APPLICATIONS

This application is a continuation of U.S. application Ser. No. 16/315,183, filed on Jan. 4, 2019, which is a U.S. National Phase application under 35 U.S.C. § 371 of International Application No. PCT/EP2017/066981, filed on Jul. 6, 2017, which claims the benefit of European Patent Application No. 16178132.3, filed on Jul. 6, 2016. These applications are hereby incorporated by reference herein.

FIELD OF THE INVENTION

The present disclosure is directed generally to health care. More particularly, but not exclusively, various methods and apparatus disclosed herein relate to monitoring bone characteristics for conditions such as osteoporosis and/or periodontitis.

BACKGROUND OF THE INVENTION

Osteoporosis is a skeletal disorder characterized by low bone mass and micro-architectural deterioration of bone tissues. Osteoporosis may be evidenced by lower than peak bone mass and/or greater than normal bone loss. It may lead to enhanced bone-fragility, which in turn may increase the risk of bone fracture, including non-traumatic and/or spontaneous fracture. Osteoporosis is the most common cause of bone fracture in elderly patients. In most instances there are few if any symptoms prior to the bone fracture. Osteoporosis may have various causes. For example, bone loss may increase in female patients after menopause as a result of lowering estrogen levels. Other causes may include alcoholism, anorexia, hyperthyroidism, surgical removal of ovaries, kidney disease, insufficient exercise, smoking, and certain medications. Osteoporosis may be diagnosed in some instances when a patient has a bone density that is 2.5 standard deviations below that of a typical young adult.

Early detection of bone loss may aid in treatment, e.g., using bisphosphonates or hormonal treatments to slow down the rate of bone decrease. However, existing techniques and devices for detecting bone loss tend to be invasive, expensive, and/or typically only available in medical offices. For example, dual-energy x-ray absorptiometry (DEXA) may be used to measure bone mineral density ("BMD"). However, it requires the use of a DEXA device that is not suitable for use in a home environment due to cost, maintenance, size, and exposure to potentially harmful x-rays. Additionally, there is some debate as to whether BMD is an accurate predictor of osteoporosis. Quantitative ultrasound ("QUS") may also be employed, e.g., to measure bone density at the patient's heel and/or wrist bone, but again is not practical for home use.

SUMMARY OF THE INVENTION

The present disclosure is directed to methods and apparatus for monitoring bone characteristics for conditions such as osteoporosis and/or periodontitis. It is generally agreed in the medical community that there is a correlation between systemic osteoporosis and jaw or mandible osteoporosis. Accordingly, various techniques are described herein for enabling regular (e.g., periodic), non-obtrusive, non-invasive, non-radiation-based, easy-to-conduct self/home-monitoring assessment of mandible bone density and composition as a proxy for systemic bone density and composition, e.g., to provide systemic osteoporosis monitoring.

In various implementations, non-obtrusive, non-invasive, easy-to-use items commonly found in bathrooms, such as dental hygiene appliances (e.g., toothbrushes, water picks, etc.), retainers, pacifiers, or appliances such as electric shavers, may be equipped with various types of sound and/or light emitters and/or sensors. These emitters/sensors may be configured to emit light waves either with or without sound waves towards a user's mandible and to detect corresponding light waves either with or without sound waves that propagate away from the mandible. These detected light waves either with or without sound waves may be analyzed to determine mandible bone density and/or composition, which as noted above may serve as a proxy for systemic bone density/composition. Incorporating such technology into an everyday item such as a toothbrush or shaver may facilitate routine monitoring as the device is used frequently. It would also allow for non-obtrusive and non-invasive measurements. Moreover, data-sharing between sensors implemented in the device and one or more remote computing devices may be accomplished using various "off-the-shelf" communication technologies.

Generally, in one aspect, a system comprising: a dental hygiene appliance comprising a handle adapted to be held by a user; a tool secured to the handle and operable by the user to perform a dental hygiene-related task; an infrared irradiator mounted on the dental hygiene appliance to emit infrared radiation towards a mandible of the user; an infrared sensor mounted on the dental hygiene appliance to detect responsive infrared radiation that is influenced by absorption of infrared irradiation by the mandible; and a controller communicatively coupled with the infrared irradiator and the infrared sensor, the controller configured to: operate the infrared irradiator to emit infrared radiation towards the mandible for a predetermined amount of time; receive, from the infrared sensor one or more signals indicative of the detected responsive infrared radiation; and determine, based on the one or more signals, one or more bone characteristics of the user.

In some embodiments, the dental hygiene appliance may take the form of a electronic toothbrush, and the tool may be a brush. In some embodiments, the controller may be integral with the dental hygiene appliance. In some embodiments, the dental hygiene appliance may include a wireless communication interface, and the may be is in wireless communication with the one or more sensors via the wireless communication interface.

In some embodiments, the controller may be configured to provide a feature vector extracted from the one or more signals to a trained machine learning model. The trained machine learning model may output a label indicative of one or more bone characteristics of the user. In various embodiments, the label may indicate that the user suffers from osteoporosis or is at risk of osteoporosis.

In some embodiments, the controller may be configured to apply Fourier Transform spectroscopy to analyze scattered infrared radiation that propagates from the mandible in response to infrared irradiation emitted by the infrared irradiator. In some embodiments, the system further includes one or more ultrasound emitters and one or more ultrasound sensors, which together form an ultrasound transceiver. In some embodiments, the controller may be configured to: operate the ultrasound transceiver to emit ultrasound waves towards the mandible; and analyze a signal produced by the ultrasound transceiver to measure a vibratory response to the emitted ultrasound waves. In some embodiments, at least one of the one or more emitters is an ultrasound insonator and at least one of the one or more sensors is an ultrasound sensor. In some embodiments, the controller may be configured to: operate the ultrasound insonator to pass ultrasound waves through the mandible towards the ultrasound sensor; and determine, based on a signal from the ultrasound sensor, a speed at which the ultrasound waves passed through the mandible or a measure of attenuation in the ultrasound waves caused by the mandible.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure.

DETAILED DESCRIPTION OF EMBODIMENTS

Osteoporosis is a skeletal disorder characterized by low bone mass and micro-architectural deterioration of bone tissues. In many cases there are few symptoms prior to bone fracture. Early detection of bone loss may aid in treatment, but existing techniques and devices for detecting bone loss tend to be invasive, expensive, and/or typically only available in medical offices. Thus, there is a need in the art to provide a non-obtrusive, non-invasive, easy-to-use, and inexpensive way to regularly (e.g., daily, weekly, semi-daily, etc.) monitor bone characteristics. In view of the foregoing, various embodiments and implementations of the present disclosure are directed to non-invasively monitoring bone characteristics for conditions such as osteoporosis.

Figure 1:
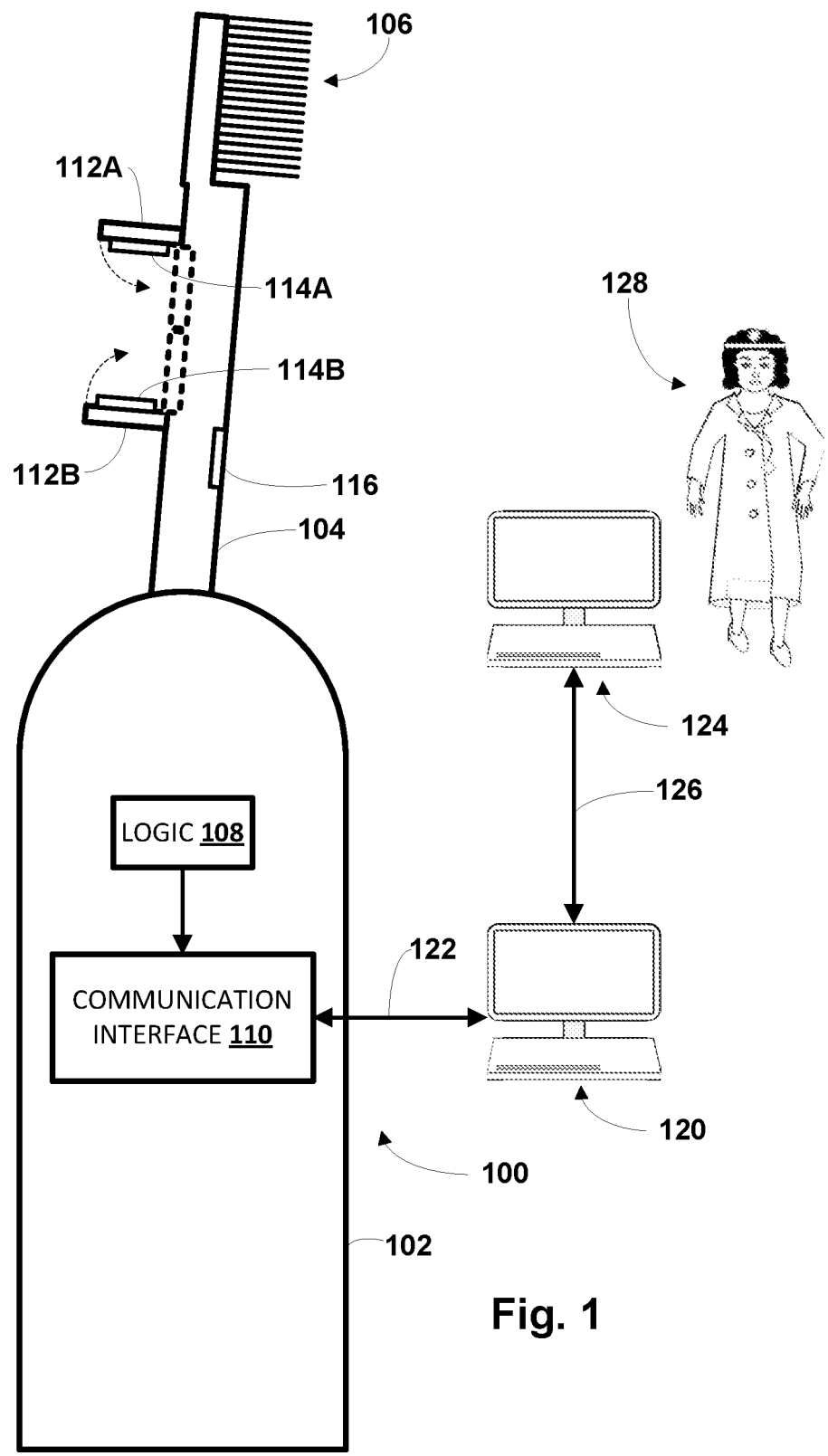
FIG. 1 illustrates an example environment in which disclosed techniques may be practiced, in accordance with various embodiments.

Referring to FIG. 1, in one embodiment, a dental hygiene appliance is depicted with selected aspects of the present disclosure in the form of an electronic toothbrush 100. Electronic toothbrush 100 includes a handle 102 adapted to be held by a user (not depicted), a neck 104 connected to handle 102, and a tool in the form of a brush 106 at an end of neck 104 opposite handle 102. While the dental hygiene appliance depicted in FIG. 1 is an electronic toothbrush, this is not meant to be limiting. In various embodiments, other dental- and non-dental-related appliances may be configured with selected aspects of the present disclosure, including but not limited to non-electric toothbrushes, shavers, water picks, pacifiers, retainers, and so forth. In some embodiments, a device intended solely for bone monitoring—and not for any other dental-hygiene related task—may be configured with selected aspects of the present disclosure.

In various embodiments, toothbrush 100 may include internal logic 108 and, in some cases, one or more communication interfaces 110 operably coupled with logic 108. Logic 108 may take various forms. In some embodiments, logic 108 takes the form of one or more processors operably coupled with memory (not depicted). The memory may store instructions that may be executed by the one or more processors to perform selected aspects of the present disclosure. In other embodiments, logic 108 may take other forms, such as a field-programmable gate array ("FPGA") and/or an application-specific integrated circuit ("ASIC"). Communication interface 110 may include one or more modules for enabling logic 108 to communicate with one or more remote computing devices. Communication interface 110 may employ various wired and/or wireless communication technologies, including but not limited to Wi-Fi, Bluetooth, near field communication ("NFC"), Edge, Ethernet, universal serial bus ("USB"), variations of cellular technology, and so forth.

In some embodiments, toothbrush 100 may include a pair of retractable members 112A and 112B. Retractable members 112A and 112B may be retractable (as shown by the arrows) between a first configuration depicted in dashed lines in which each retractable member 112 is substantially flush with a surface of toothbrush 100 (in this case, flush with a surface of neck 104) and a second configuration depicted in solid line in which each retractable member 112 extends transversely from the surface of toothbrush 100. In various embodiments, retractable members 112A and 112B may be spaced from each other by a predetermined distance that is selected so that retractable members 112A and 112B in the second configuration are sufficiently far apart that they can be positioned to flank (i.e. be on opposite sides of) the user's mandible.

Toothbrush 100 may include one or more emitters to emit one or more sound or light waves towards a mandible of the user, and one or more sensors to detect one or more sound or light waves propagating away from the mandible. The detected one or more sound or light waves may either originate from, or be caused by, the emitted one or more waves. For example, in FIG. 1, toothbrush 100 includes an emitter 114A mounted on first retractable member 112A and a sensor 114B mounted on second retractable member 112B. Emitter 114A may emit sound or light waves towards sensor 114B. Sensor 114B may detect the emitted sound or light waves.

In various embodiments, the user may extend retractable members 112A and 112B to the second configuration depicted in solid lines, and then position toothbrush 100 so that first retractable member 112A (and hence, emitter 114A) is on one side of the user's mandible, and second retractable member 112B (and hence, sensor 114B) is on an opposite side of the user's mandible. That way, sound or light waves emitted by emitter 114A pass through the user's mandible before being detected by sensor 114B. As will be described in more detail below, logic 108 may analyze a signal provided by sensor 114B to detect any changes or influences on the waves caused by the user's mandible. These changes or influences may be indicative of one or more bone characteristics of the user.

In FIG. 1, toothbrush 100 includes an additional emitter/sensor pair that together form a transceiver 116. Transceiver 116 may emit sound and/or light waves towards the user's mandible, and may detect responsive sound or light waves that propagate from the user's mandible. For example, in some implementations, transceiver 116 may insonate the user's mandible with ultrasound waves and then detect a vibratory response. In other implementations, transceiver 116 may irradiate the user's mandible with infrared radiation and then detect wavelength-dependent absorption of emitted light waves. In some embodiments, toothbrush 100 may be equipped with multiple transceivers (or another emitter/sensor pair), one to emit/detect infrared radiation and another to emit/detect ultrasonic waves.

In various embodiments, logic 108 may be configured to receive, from one or more sensors (e.g., 114B, 116), one or more signals indicative of waves detected propagating from a user's mandible. Logic 108 may then be configured to determine, based on the one or more signals, one or more bone characteristics of the user. In some embodiments, logic 108 may provide data indicative of its analysis over a wireless connection (e.g., facilitated by communication interface 110) to a remote computing device 120, which may be a computing device owned or operated by the user. Remote computing device 120 may take various forms, such as a smart phone, a tablet computer, a smart watch, a laptop computer, a desktop computer, a set top box, and so forth. In some embodiments, remote computing device 120 may provide various audible, visual, and/or tactile feedback to the user based on the analysis performed by logic 108. For instance, if logic 108 (or remote computing device 120) determines, based on signals from sensor 114B and/or transceiver 116, that the user is experiencing excessive bone loss (e.g., by comparing a current measurement to one or more prior measurements), computing device 120 may render a warning to the user to visit their health care provider.

In some embodiments, remote computing device 120 may be communicatively coupled with a health care provider computing device 124 over one or more wired or wireless network connections 126 (e.g., the Internet). Health care provider computing device 124, which may take one or more of the various form factors mentioned above, may be operated by one or more health care providers 128. Health care provider computing device 124 may provide various types of audio, visual, and/or haptic feedback to health care provider 128 that indicate one or more bone characteristics of the user. Based on this feedback, health care provider 128 may take various responsive actions, such as initiating treatment, advising lifestyle changes, etc.

As noted above, various types of emitters and/or sensors may be employed, alone or in combination, in order to detect bone characteristics of the user. For example, some emitters take the form of ultrasound emitters or transceivers that generate high-frequency ultrasound waves to be propagated towards the user's mandible upon holding the transceiver against the mandible for a predetermined amount of time. The signal detected by the transceiver or a separate sensor may represent the bone vibrational response, and may carry information regarding bone composition and/or density.

Figure 2:
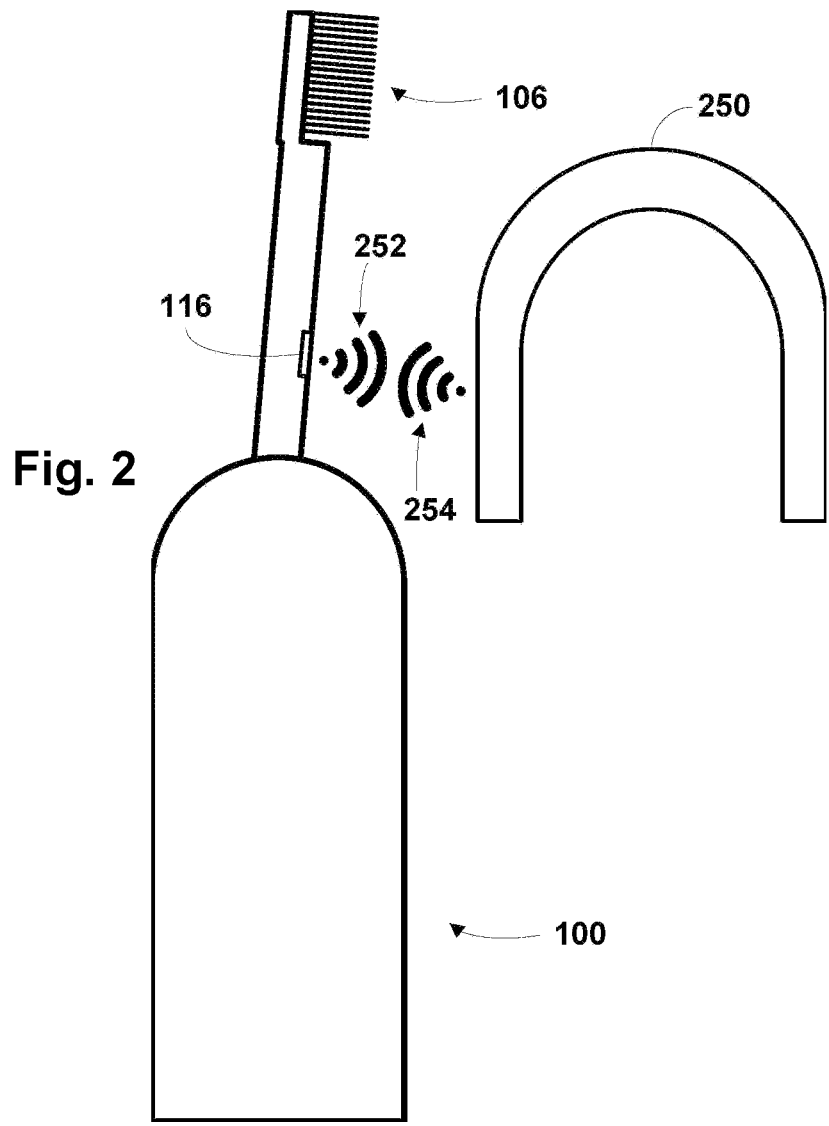
FIG. 2 depicts an example dental appliance assembly being used to detect bone characteristics in a mandible using ultrasound and vibratory response.

FIG. 2 depicts an example of how ultrasound waves may be used to determine one or more bone characteristics. Toothbrush 100 includes an ultrasound transceiver 116. Toothbrush 100 has been brought into position such that ultrasound transceiver 116 is adjacent (e.g., touching, within a predetermined distance of) the user's mandible 250. Ultrasound transceiver 116 emits outgoing ultrasound waves 252 and receives responsive incoming ultrasound waves 254. Responsive incoming ultrasound waves 254 may be analyzed by logic (108, see FIG. 1) to determine a vibratory response. The vibratory response may be influenced by, among other things, bone density and/or composition of the user's mandible. Logic 108 may then analyze a signal produced by transceiver 116 to determine bone characteristics. For example, logic 108 may identify a trend in which the vibratory response increases over time, suggesting that the user's bone density is decreasing.

Another example of how ultrasound waves may be used to determine one or more bone characteristics is depicted in FIG. 1. Suppose emitter 114A is an ultrasound emitter (or transceiver, may also be referred to as an "ultrasound insonator") and sensor 114B is an ultrasound sensor (or transceiver). In various embodiments, once toothbrush 100 is positioned so that a portion of the user's mandible (250, see FIG. 2) is between emitter 114A and sensor 114B, emitter 114A may emit ultrasound waves towards sensor 114B. The signal produced by sensor 114B in response to these detected waves may provide information about, for instance, a speed at which the ultrasound waves passed through the mandible, or a measure of attenuation from the ultrasound waves originally emitted from emitter 114A. These parameters may be used, e.g., by logic 108, to estimate the user's BMD. Whether the ultrasound configuration depicted in FIG. 2 or FIG. 1 is used, each measurement may be analyzed, and/or measurements over time may be analyzed, e.g., to identify trends in bone loss/composition/density.

Figure 3:
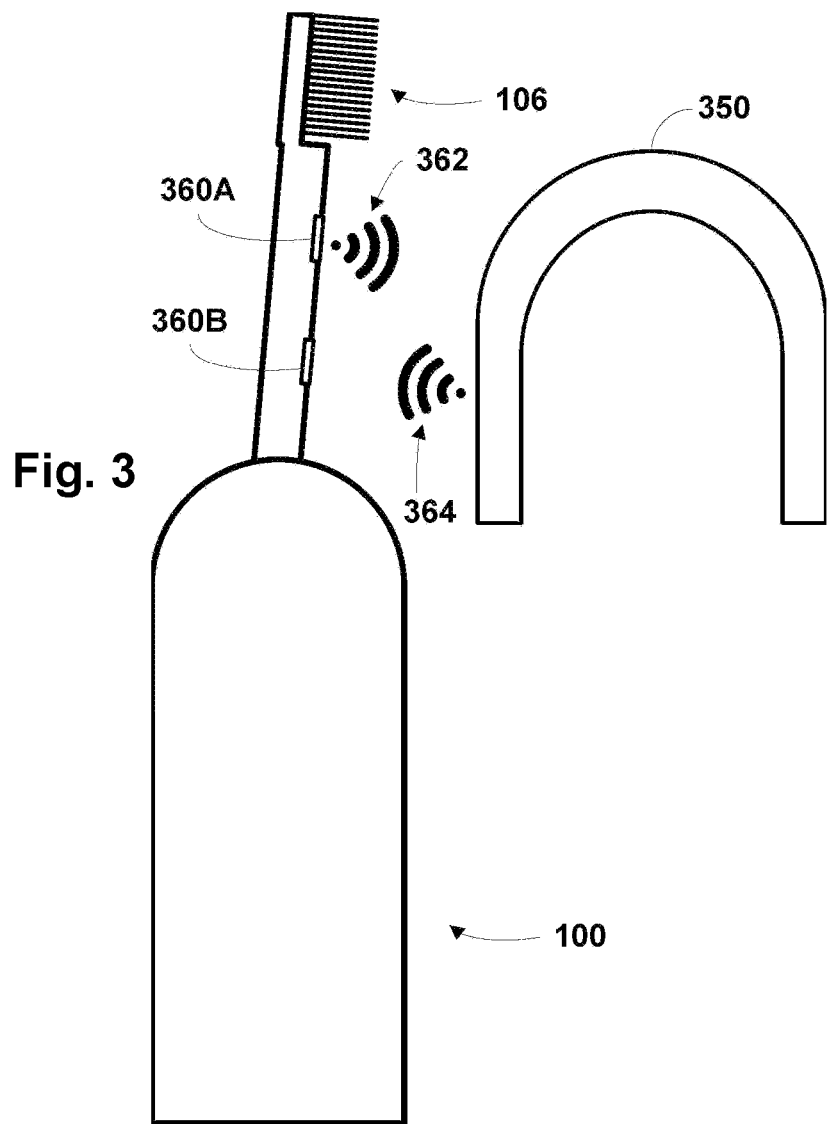
FIG. 3 depicts an example dental appliance assembly being used to detect bone characteristics by irradiating a mandible with infrared radiation and observing responsive irradiation.

FIG. 3 depicts an example of how infrared waves may be used to determine one or more bone characteristics. In this example, toothbrush 100 includes an infrared emitter 360A (also referred to as an "irradiator") to emit infrared radiation 362 towards a user's mandible 350 and an infrared sensor 360B that is configured to detect responsive infrared radiation 364 propagating from mandible 350. In this example, emitter 360A and sensor 360B are offset from each other, rather than being formed together (as was the case with ultrasound emitter/sensor 116 in FIG. 2), but this is not required. In other embodiments, a single component, such as a light emitting diode ("LED") may be configured to both emit and detect infrared radiation. Infrared radiation 362 emitted by emitter 360A towards mandible 350 may, upon entering mandible 350, be scattered in various different directions. At least some of this scattered infrared radiation may be directed towards, and hence detected by, sensor 360B, e.g., as indicated at 364.

In some embodiments, such as that depicted in FIG. 3, infrared emitter 360BA and sensor 360B may take the form of a near-infrared spectroscopy device. Mandible 350 may be irradiated with infrared radiation 362 for a specified amount of time (e.g., as instructed by an audio and/or visual output) once one or both of emitter 360A and sensor 360B are pressed against mandible 350. In some embodiments, Fourier transform infrared ("FTIR") spectroscopy techniques may be employed, e.g., by logic 108, to detect absorption of infrared radiation during vibrational transitions in covalently bound atoms. This detected absorption may be analyzed to determine various bone characteristics that influence so-called "bone quality." These bone characteristics may include factors influencing the geometric and/or material properties that contribute to bone fracture resistance. Geometric properties may include macroscopic geometry of the whole of mandible 350 and microscopic architecture of bone components. Material properties may include the composition and arrangement of primary constituents of bone tissue, such as collagen and minerals, as well as microdamage and/or microstructural discontinuities. FTIR imaging may provide information on bone constituents at molecular level, and can thus be used as a tool to assess bone quality.

Various bone characteristics determined using the aforementioned techniques may be analyzed in various ways to determine bone health of a patient. In some implementations, a machine learning model may be trained to receive a feature vector extracted from various sensor signals described above and provide output including labels such as "osteoporosis detected," "osteoporosis risk detected," "no osteoporosis detected," and so forth. A machine learning model may be implemented using various techniques, including but not limited to logistic regression models or neural networks. Such a machine learning model may be trained on various types of positive and/or negative training examples. Positive training examples may include, for instance, feature vectors associated with patients known to have healthy bone density and/or composition (who therefore do not exhibit osteoporosis). Negative training examples may include, for instance, feature vectors associated with patients known to have unhealthy bone density and/or composition, such as osteoporosis patients.

In some implementations, when a healthy user first begins using a device such as a toothbrush configured with selected aspects of the present disclosure, the user may establish a healthy "baseline" of one or more bone characteristics (e.g., bone density, bone composition), e.g., by using the device as described above. Data acquired after each subsequent use may then be compared to earlier data to determine whether, for instance, any trends can be identified relating to bone loss, composition degradation, and so forth.

While the particular embodiments described above have each included a particular number of emitters and/or sensors, this is not meant to be limiting. Any combination of any number of sound and/or light emitters/sensors may be employed on a single device to obtain various levels of information about the user's bone quality. For example, in some embodiments, both types of ultrasound emitters sensors described above (e.g., 114A/114B in combination with 116) may be employed together. An infrared emitter/sensor (e.g., 360A/360B) may also be employed in combination with one or both types of ultrasound emitters/sensors, or by itself.

Evaluation of the bone both by means of reflection of ultrasound waves and by spectral analysis of infrared light reflected by bone provides insight into different characteristics and properties of bone. Combination of these two technologies would add to gaining a better understanding of the quality of the researched bone. Ultrasound would enable verification of the bone on a macroscale by assesing vibrational response of the bone while the spectral infrared technology would allow for analysing molecular composition of the bone, thus the combination of the infrared emitter/sensor (360A/360B) and ultrasound emitter/sensor (114A/114B, 116) facilitates analysis of two different characteristics of the bone allowing for a more accurate diagnosis. Evaluation of two different parameters provides better insight into the quality of bone, i.e not only bone density, but also quality of bone, which in effect provides better prediction of fracture risk.

Figure 4:
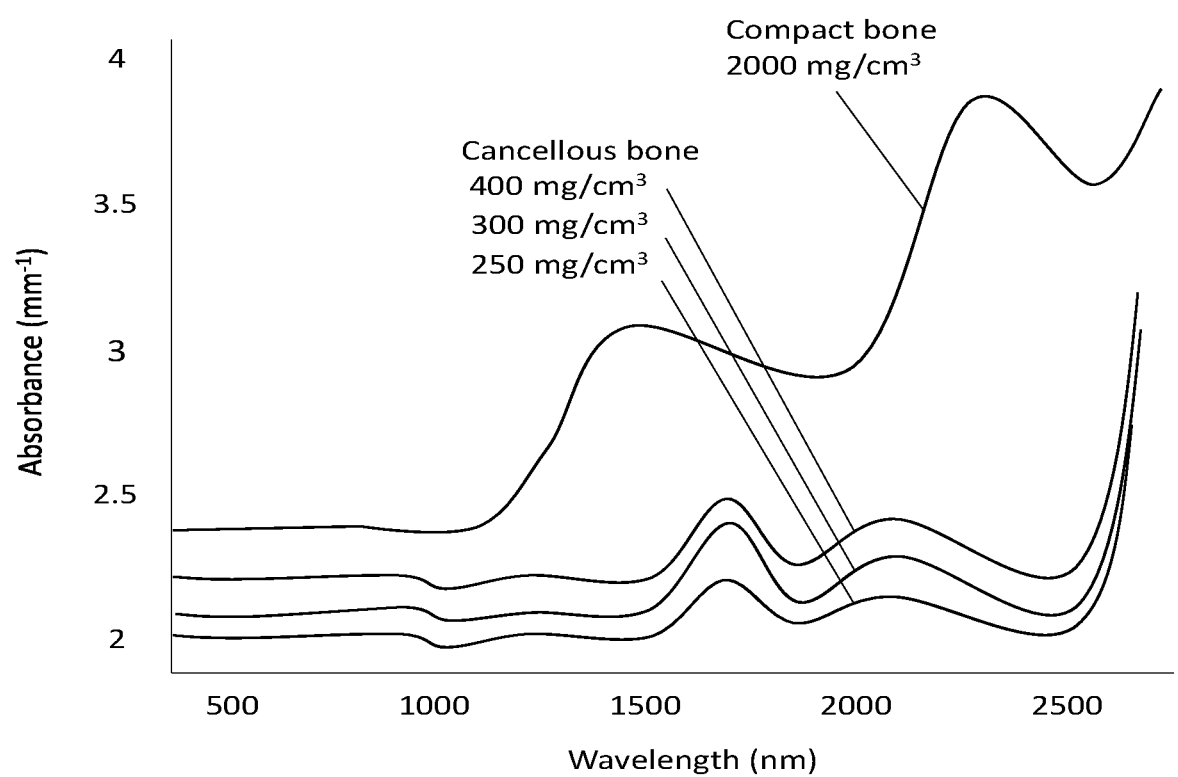
FIG. 4 depicts an example graph depicting absorbance in various infrared wavelengths caused by various bone characteristics, in accordance with various embodiments.

FIG. 4 depicts an example graph depicting absorbance in various infrared wavelengths caused by various bone characteristics, in accordance with various embodiments. The X axis represents infrared wavelengths in nm and the Y axis represents absorbance in $mm^{-1}$. The top line represents so-called "compact" or "cortical" bone. Cortical bone is much denser (e.g., 2000 $mg/cm^3$) than the so-called "cancellous" or "trabecular" bone represented by the bottom three lines, which range from 250 to 400 $mg/cm^3$. Cortical bone is typically found near bone exteriors. Cancellous bone is typically found near the ends of long bones, near joins, and within vertebrae interiors. Cancellous bone is more severely affected by osteoporosis than cortical bone. The example graph shows how the absorbance of the infrared light waves by bone changes as the density and calcium content of the cancellous bone lowers due to osteoporosis progression.

Figure 5:
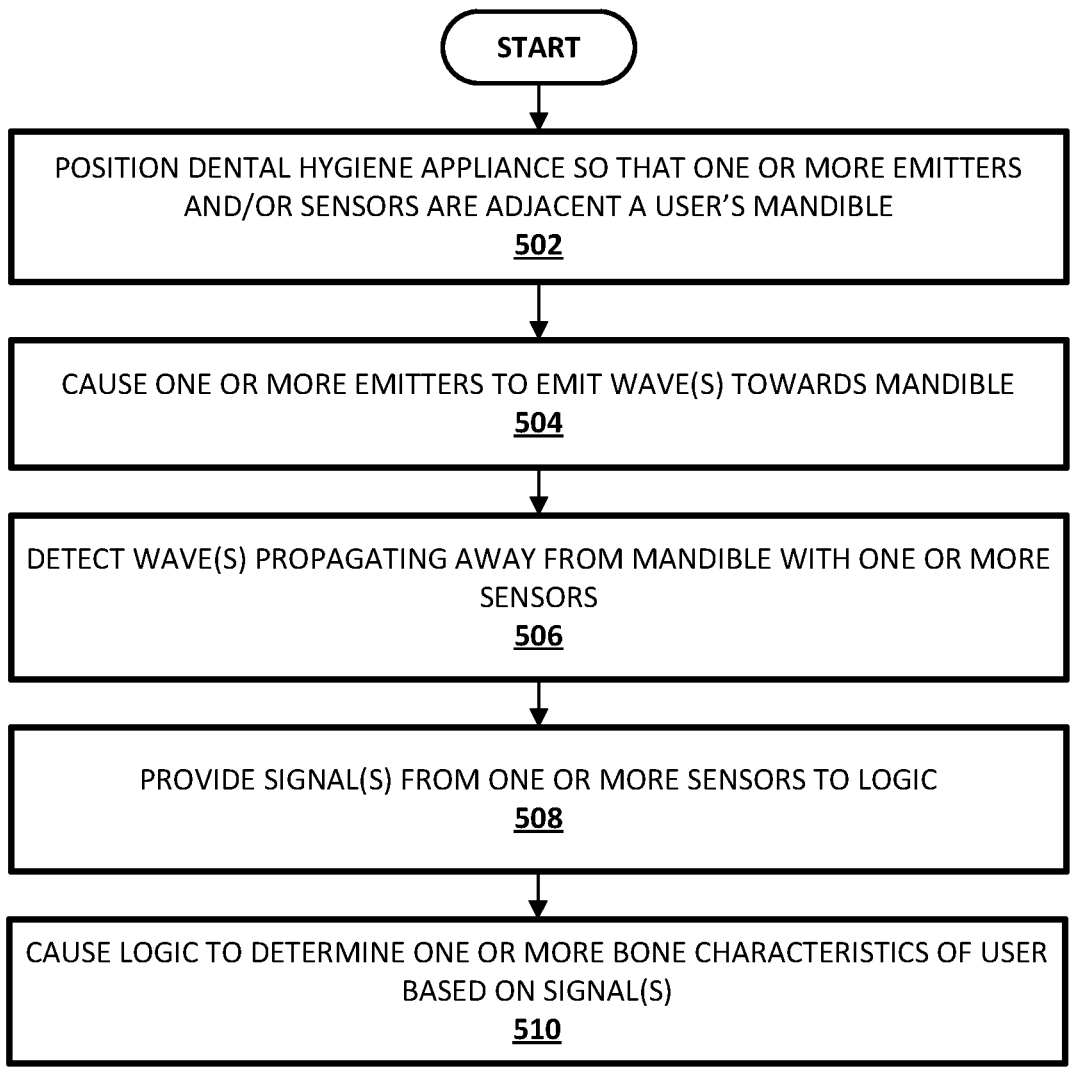
FIG. 5 depicts an example method of non-invasively monitoring bone characteristics for conditions such as osteoporosis, in accordance with various embodiments.

FIG. 5 depicts one example method 500 for non-invasively monitoring bone characteristics for conditions such as osteoporosis, in accordance with various embodiments. While operations of method 500 are depicted in a particular order, this is not meant to be limiting. Various operations may be added, omitted, or reordered.

At block 502, a user may position a dental hygiene appliance (or another appliance meant to be used periodically by a user, such as a shaver, a water pick, a retainer, etc.) so that one or more emitters and/or sensors are adjacent the user's mandible. For example, in FIG. 1, toothbrush 100 may be positioned so that retractable members 112A and 112B (and hence, emitter 114A and sensor 114B) are on opposite sides (i.e. flank) the user's mandible. Or, toothbrush 100 may be positioned so that neck 104 and transceiver 116 are positioned adjacent to (e.g., touching, within a predetermined distance of, etc.) of the user's mandible. In some embodiments, the operations of block 502 may occur contemporaneously with performance of a dental hygiene-related task, although this is not required.

In some embodiments, the user may position the appliance suitably in response to audible and/or visual instructions provided by, for instance, the appliance itself and/or a nearby computing device (e.g., 120). For example, toothbrush 100 may be paired (e.g., using Bluetooth) with a user's smart phone, tablet, smart mirror, etc. A user may initiate an application on the paired device that provides instructions to the user on brushing his or her teeth. The application may also provide output instructing the user to position toothbrush 100 as described above, e.g., before or after brushing. For example, the user may be instructed to place neck 104 against their lower left or right jaw onto their gums and below their teeth. Once toothbrush 100 is properly positioned, the user may initiate emission of light or sound waves for a predetermined time interval, e.g., by pressing an actuator. In some embodiments, the paired device or toothbrush 100 may provide audio, visual, and/or haptic feedback indicating that the predetermined time interval is up (or that adequate measurement has been captured), so that the user may remove toothbrush from his or her jaw. In some embodiments, if the measurements taken are inadequate (e.g., the user moved toothbrush 100 during measurement), the paired device or toothbrush 100 may instruct the user to reinitiate measurement.

In some embodiments, toothbrush 100 may include an actuator (not depicted, e.g., a button or pressure release underneath retractable members 112A and 112B) that is operable to transition retractable members 112A and 112B between the first and second configurations depicted in FIG. 1. The user may operate the actuator, for instance, after the user finishes brushing his or her teeth, e.g., so that retractable members 112A and 112B are not in the way while brushing. In some embodiments, retractable members 112A and 112B may automatically extend from toothbrush into the second configuration, e.g., after a preprogrammed brushing routine has been completed.

At block 504, logic 108 may cause one or more emitters (e.g., 114A, 116, 360A) to emit light waves with or without sound waves towards the user's mandible, e.g., for a predetermined amount of time. For example, once the user has properly positioned toothbrush 100 as described above, the user may press a button that causes the emission to commence, e.g., for a few seconds, etc. At block 506, the light waves further with or without sound waves propagating away from the user's mandible may be detected by one or more sensors (e.g., 114B, 116, 360B).

At block 508, a signal indicative of the light waves with/without one or more sound waves detected at block 506 may be provided, e.g., by one or more sensors (e.g., 114B, 116, 360B) to logic 108. At block 510, logic 108 may analyze the signals as described above to determine one or more bone characteristics of the user. As noted above, these bone characteristics may include but are not limited to bone density, composition, and so forth. In some embodiments, rather than logic 108 integral with toothbrush 100 determining the bone characteristics, logic 108 may simply provide data indicative of the sensor signals to one or more remote computing devices (e.g., 120, 124). This may particularly be the case where toothbrush 100 is a resource-constrained device that may lack sufficient processing capabilities and/or battery power to perform the calculations itself.

Figure 6:
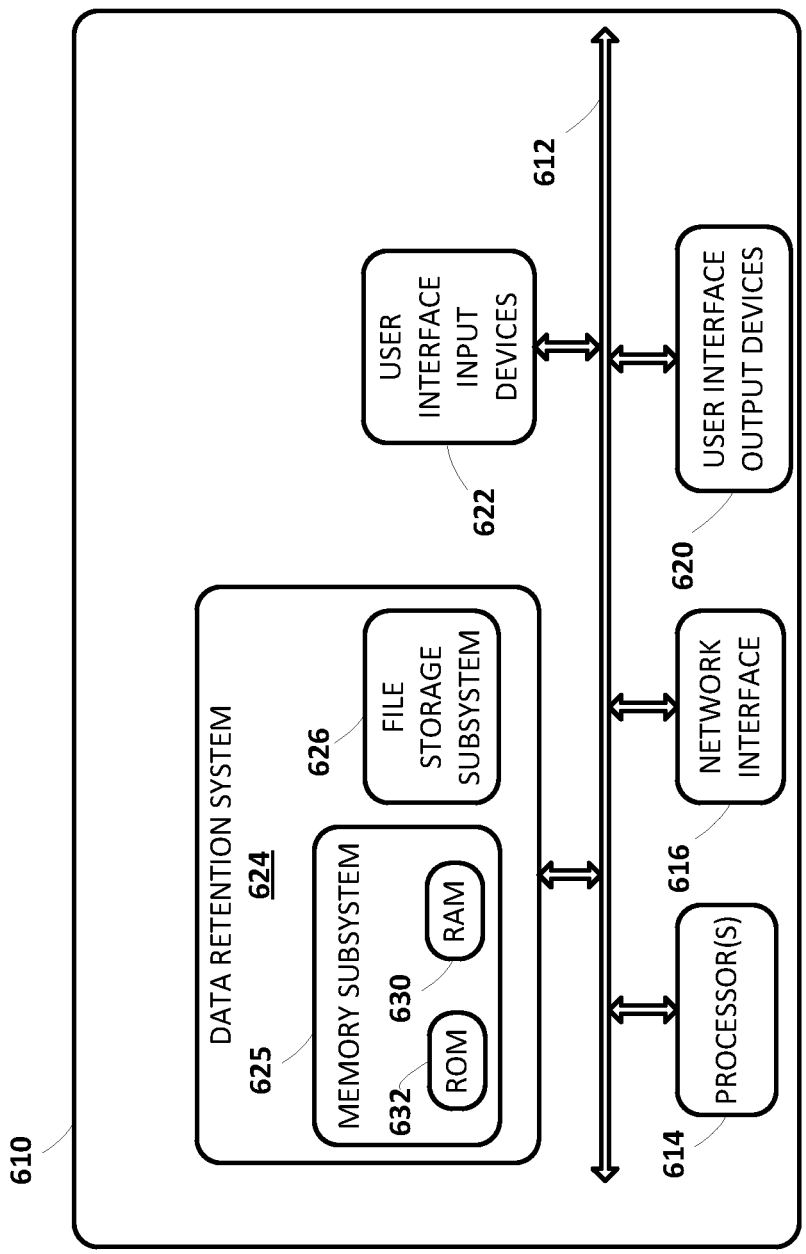
FIG. 6 depicts an example computer system.

FIG. 6 is a block diagram of an example computer system 610. Computer system 610 typically includes at least one processor 614 which communicates with a number of peripheral devices via bus subsystem 612. As used herein, the term "processor" will be understood to encompass various devices capable of performing the various functionalities attributed to various components described herein such as, for example, microprocessors, FPGAs, ASICs, other similar devices, and combinations thereof. These peripheral devices may include a data retention subsystem 624, including, for example, a memory subsystem 625 and a file storage subsystem 626, user interface output devices 620, user interface input devices 622, and a network interface subsystem 616. The input and output devices allow user interaction with computer system 610. Network interface subsystem 616 provides an interface to outside networks and is coupled to corresponding interface devices in other computer systems.

User interface input devices 622 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 610 or onto a communication network.

User interface output devices 620 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 610 to the user or to another machine or computer system.

Data retention system 624 stores programming and data constructs that provide the functionality of some or all of the modules described herein. For example, the data retention system 624 may include the logic to perform selected aspects of method 500, and/or to implement one or more components of toothbrush 100, remote computing device 120, and/or health care provider computing device 124.

These software modules are generally executed by processor 614 alone or in combination with other processors. Memory 625 used in the storage subsystem can include a number of memories including a main random access memory (RAM) 630 for storage of instructions and data during program execution, a read only memory (ROM) 632 in which fixed instructions are stored, and other types of memories such as instruction/data caches (which may additionally or alternatively be integral with at least one processor 614). A file storage subsystem 626 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 626 in the data retention system 624, or in other machines accessible by the processor(s) 614. As used herein, the term "non-transitory computer-readable medium" will be understood to encompass both volatile memory (e.g. DRAM and SRAM) and non-volatile memory (e.g. flash memory, magnetic storage, and optical storage) but to exclude transitory signals.

Bus subsystem 612 provides a mechanism for letting the various components and subsystems of computer system 610 communicate with each other as intended. Although bus subsystem 612 is shown schematically as a single bus, alternative implementations of the bus subsystem may use multiple busses.

Computer system 610 can be of varying types including a workstation, server, computing cluster, blade server, server farm, or any other data processing system or computing device. In some embodiments, computer system 610 may be implemented within a cloud computing environment. Due to the ever-changing nature of computers and networks, the description of computer system 610 depicted in FIG. 6 is intended only as a specific example for purposes of illustrating some implementations. Many other configurations of computer system 610 are possible having more or fewer components than the computer system depicted in FIG. 6.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

The invention claimed is:

1. A system comprising:
   a dental appliance;
     an infrared irradiator mounted on the dental appliance to emit infrared radiation towards a mandible of the user;
     an infrared sensor mounted on the dental appliance to detect responsive infrared radiation that is influenced by absorption of infrared irradiation by the mandible; and
   a controller communicatively coupled with the infrared irradiator and the infrared sensor, the controller configured to:
   operate the infrared irradiator to emit infrared radiation towards the mandible for a predetermined amount of time;
   receive, from the infrared sensor one or more signals indicative of the detected responsive infrared radiation and
   determine, based on the one or more signals, a bone characteristic of the user.

2. The system of claim 1 wherein the dental appliance comprises a toothbrush.

3. The system of claim 2 wherein the infrared irradiator and the infrared sensor are mounted to the toothbrush on respective retractable members spaced from each other by a predetermined distance, wherein each retractable member is retractable between a first configuration in which the retractable member is substantially flush with a surface of the toothbrush and a second configuration in which the retractable member extends transversely from the surface of the toothbrush, wherein the predetermined distance is selected so that the retractable members in the second configuration are spaced to flank the user's mandible.

4. The system of claim 1 wherein the dental appliance comprises a water pick.

5. The system of claim 1 wherein the controller is integral with the dental appliance.

6. The system of claim 1 wherein the dental appliance comprises a wireless communication interface and the controller is in wireless communication with the one or more sensors via the wireless communication interface.

7. The system of claim 1 wherein the controller is configured to provide a feature vector extracted from the one or more signals to a trained machine learning model, and wherein the trained machine learning model outputs a label indicative of a bone characteristic of the user.

8. The system of claim 7 wherein the label is indicative of osteoporosis.

9. The system of claim 7 wherein the label is indicative of a risk of osteoporosis.

10. The system of claim 1 wherein the controller is configured to apply Fourier Transform spectroscopy to analyze scattered infrared radiation that propagates from the mandible in response to infrared irradiation emitted by the infrared irradiator.

11. The system of claim 1 further comprising one or more ultrasound emitters and one or more ultrasound sensors together forming an ultrasound transceiver.

12. The system of claim 11 wherein the controller is configured to:
   operate the ultrasound transceiver to emit ultrasound waves towards the mandible; and
   analyze a signal produced by the ultrasound transceiver to measure a vibratory response to the emitted ultrasound waves.

13. The system of claim 1 further comprising an ultrasound insonator and an ultrasound sensor.

14. The system of claim 13 wherein the controller is configured to:
   operate the ultrasound insonator to pass ultrasound waves through the mandible towards the ultrasound sensor; and
   determine, based on a signal from the ultrasound sensor, a speed at which the ultrasound waves passed through the mandible or a measure of attenuation in the ultrasound waves caused by the mandible.

* * * * *